US00PP28734P2

(12) United States Plant Patent
Glenn

(10) Patent No.: US PP28,734 P2
(45) Date of Patent: Dec. 5, 2017

(54) ***EUPHORBIA* 'LAMB01'**

(50) Latin Name: *Euphorbia characias*
Varietal Denomination: LAMB01

(71) Applicant: David Glenn, Ascot (AU)

(72) Inventor: David Glenn, Ascot (AU)

( * ) Notice: Subject to any disclaimer, the term of this patent is extended or adjusted under 35 U.S.C. 154(b) by 0 days.

(21) Appl. No.: 15/330,070

(22) Filed: Aug. 1, 2016

(51) Int. Cl.
*A01H 5/02* (2006.01)

(52) U.S. Cl.
USPC ..... Plt./302

(58) Field of Classification Search
USPC ..... Plt./302
See application file for complete search history.

*Primary Examiner* — Annette Para
(74) *Attorney, Agent, or Firm* — Cassandra Bright

(57) ABSTRACT

A new and distinct *Euphorbia characias* cultivar named 'LAMB01' is disclosed, characterized by variegated foliage and a free flowering habit. Plants are uniquely bushy in habit. The new variety is a *Euphorbia* hybrid, typically used for ornamental horticulture purposes.

3 Drawing Sheets

Latin name of the genus and species: *Euphorbia characias.*

Variety denomination: 'LAMB01'.

BACKGROUND OF THE INVENTION

The new cultivar is the product of chance discovery by the inventor, David Glenn. The new variety was discovered as a naturally occurring mutation of the patented variety *Euphorbia characias* 'Tasmanian Tiger', U.S. Plant Pat. No. 15,715.

Asexual reproduction of the new cultivar 'LAMB01' by vegetative cuttings was performed in Australia and has shown that the unique features of this cultivar are stable and reproduced true to type in successive generations.

SUMMARY OF THE INVENTION

The cultivar 'LAMB01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LAMB01' These characteristics in combination distinguish 'LAMB01' as a new and distinct *Euphorbia* cultivar:

1. Free flowering habit.
2. Variegated foliage.
3. Bushy plant habit, with multiple lateral branches

PARENT COMPARISON

Plants of the new cultivar 'LAMB01' are similar to plants of the parent, *Euphorbia characias* 'Tasmanian Tiger' in most horticultural characteristics, however, plants of the new cultivar 'LAMB01' produce more branches per plant, producing a denser, bushier plant form. Foliage of the new variety has a thinner cream colored margin, and plants grow faster and more vigorously. Additionally, mature plants of the new variety are wider and taller than plants of the parent variety.

COMMERCIAL COMPARISON

Plants of the new cultivar 'LAMB01' are similar to plants of the commercial variety, *Euphorbia characias* 'Glacier Blue', unpatented in most horticultural characteristics, however, plants of the new cultivar 'LAMB01' are shorter and produce more branches per plant. Plants of the new variety are bushy, while plants of the comparator have an open habit.

Plants of the new cultivar 'LAMB01' are also similar to plants of the commercial variety, *Euphorbia characias* 'Silver Swan', unpatented, in most horticultural characteristics, however, plants of the new cultivar 'LAMB01' are taller at maturity. Foliage of the new variety is blue-green with a white margin, whereas foliage of 'Silver Swan' is green with a white margin.

BRIEF DESCRIPTION OF THE PHOTOGRAPHS

The accompanying photograph in FIG. 1 illustrates in full color a close-up of a typical plant of 'LAMB01' grown outdoors at approximately 2 years old.

Figure 1:
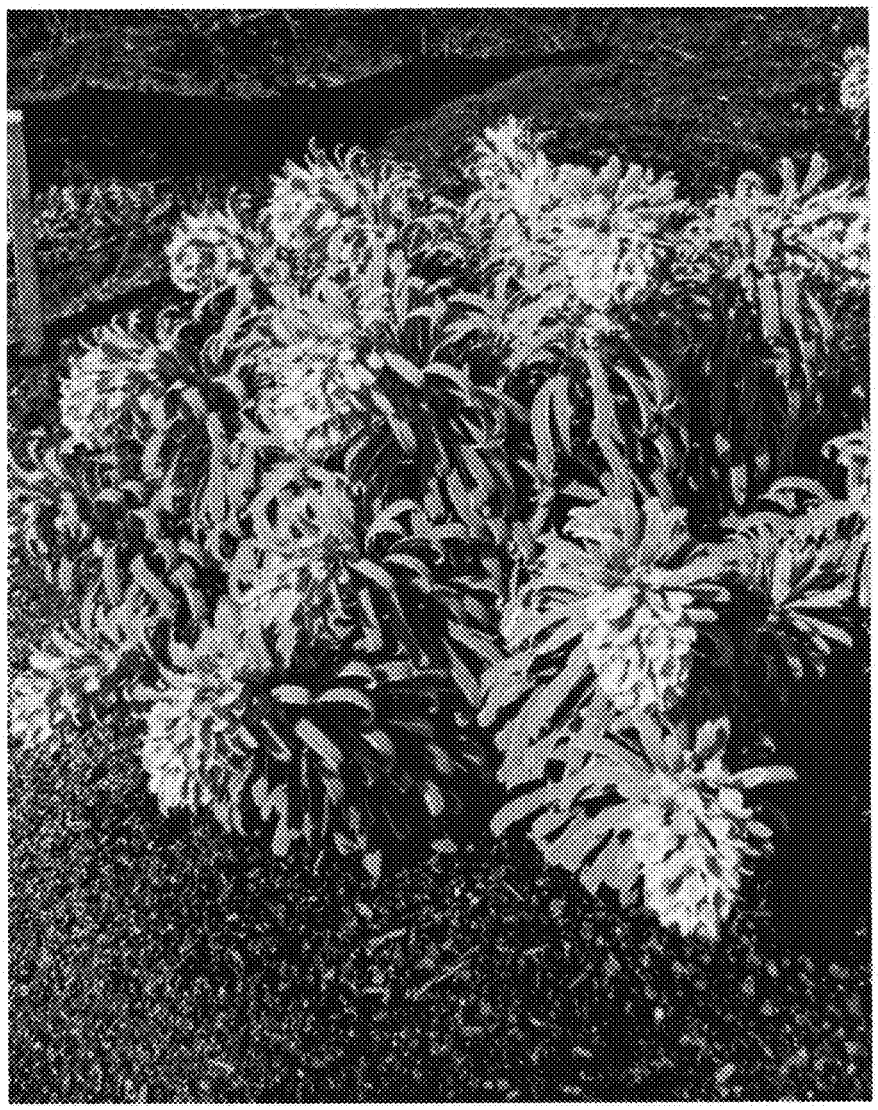
Figure 2:
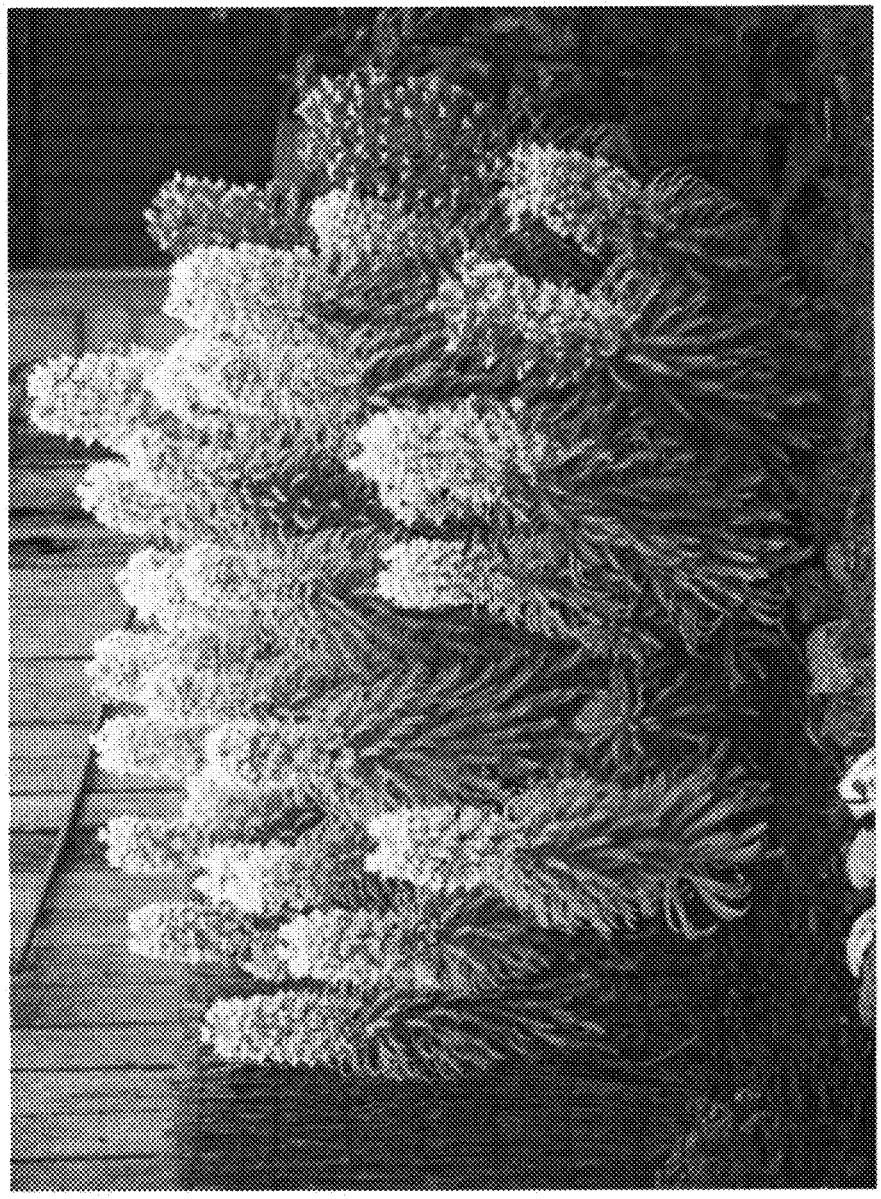
FIG. 2 illustrates a more mature plant of approximately 4 years old, grown outdoors in Australia.
Figure 3:
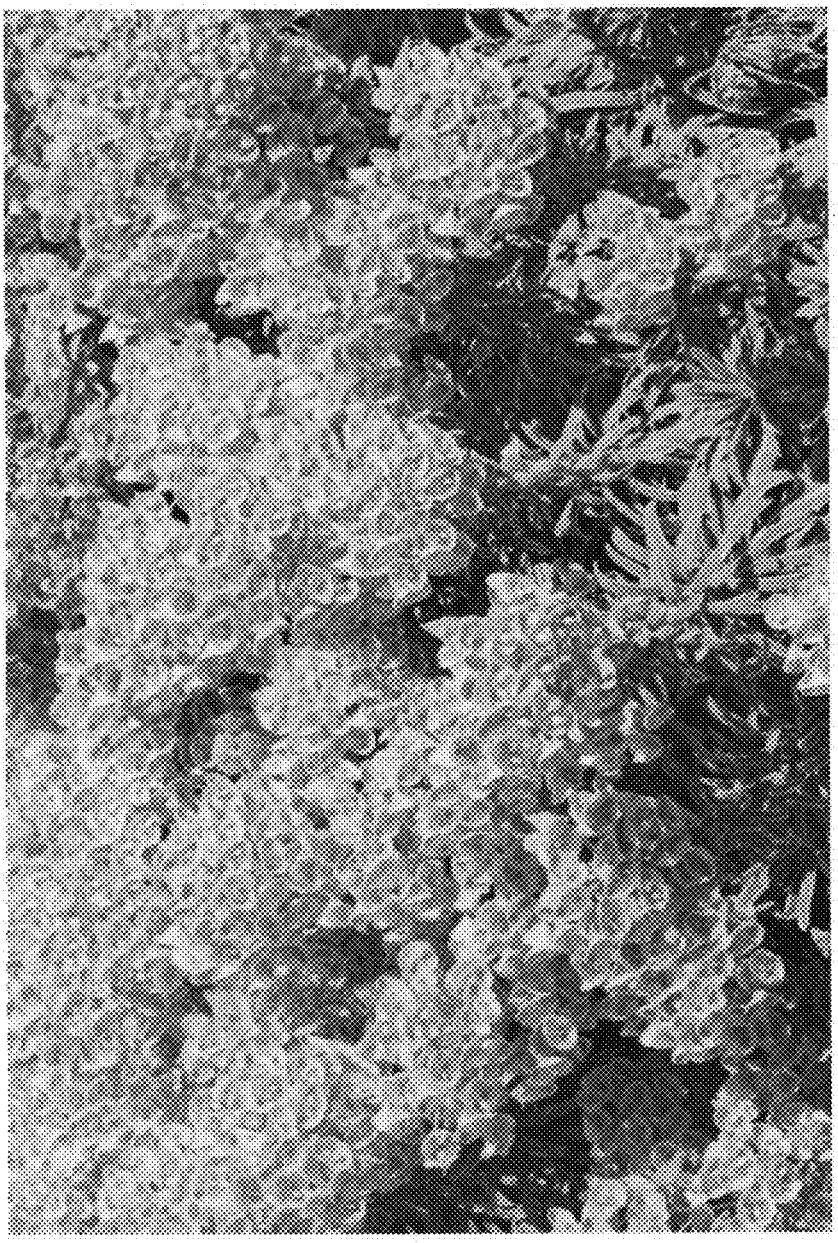
FIG. 3 illustrates in full color a close up view of typical inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'LAMB01' plants grown in a commercial greenhouse. The growing temperature ranged from approximately 9 to 14° C. at night to 21 to 29° C. during the day. Measurements and numerical values represent averages of typical flowering types. No chemical or photoperiodic treatments were given. Botanical classification: *Euphorbia characias* 'LAMB01.'

PROPAGATION

Time to rooting: 10 to 14 days at approximately 21° C.
Root description: Thick, well branched.

PLANT

Growth habit: Upright, bushy, perennial subshrub.
Height: Approximately 120 cm.
Plant spread: Approximately 120 cm.
Growth rate: Moderate.
Branching characteristics: Moderate branching.
Quantity of lateral branches: Average range 12 to 16 on a 2 year old plant.
Length of lateral branches: Approximately 25 cm.
Diameter of lateral branches: Approximately 0.5 cm.
Texture of lateral branches: Smooth, pubescence at nodes.
Internode length: Approximately 2 cm.
Strength of stem: Flexible and strong.
Color of lateral branches: Near RHS Greyed-Green 194A.
Aspect: Upright and straight.
Number of leaves per lateral branch: Approximately 40 to 60.

FOLIAGE

Leaf:
*Type*.—Simple, whorled.
*Basal leaves*.—Arrangement: Alternate, single. Average Length: Approximately 11.5 cm. Average Width: Approximately 1.8 cm. Shape of blade: Oblanceolate. Apex: Acute. Base: Truncate. Attachment: Sessile. Margin: Entire. Texture of top surface: Pubescent. Texture of bottom surface: Pubescent. Leaf internode length: Approximately 0.7 cm. Color: Young foliage upper side: Near RHS Greyed-Green 190A, margin Green-White 157D. Margin approximately 3 mm wide. Young foliage under side: Near RHS Greyed-Green 190A, margin Green-White 157D. Margin approximately 3 mm wide. Mature foliage upper side: Near RHS Greyed-Green 191C, margin Green-White 157D. Margin approximately 3 mm wide. Mature foliage under side: Near RHS Greyed-Green 191C, margin Green-White 157D. Margin approximately 3 mm wide.
*Venation*.—Type: Pinnate. Venation color upper side: Near RHS Greyed-Green 191D. Venation color under side: Near RHS Greyed-Green 191C.
Petiole: Not present.

FLOWER

Bloom period: Naturally blooming late June through mid July.
Bud:
*Bud shape*.—Spherical.
*Bud length*.—Approximately 0.05 cm.
*Bud diameter*.—Approximately 0.05 cm.
*Bud color*.—Near Yellow 1C.
Inflorescence:
*Form*.—Umbel-like compound cyme. Primary Cymes: 5-merous. Secondary Cymes: 3-merous.
*Measurement of average primary cyme*.—Diameter of entire inflorescence: Approximately 10 to 12 cm. Depth of entire inflorescence: Approximately 15 cm.
Individual flowers:
*Length*.—Approximately 2 cm.
*Width*.—Approximately 0.9 cm.
*Aspect*.—Upright.
*Duration on plant*.—Approximately 3 to 4 weeks. Persistent.
Fragrance: None.
Floral bracts:
*Arrangement*.—2 or 3 opposite or whorled, subtending cyathium.
*Shape*.—Broadly ovate.
*Apex*.—Acute.
*Base*.—Attenuate.
*Length*.—0.8 cm, average.
*Width*.—0.7 cm.
*Texture*.—Glaborous.
*Color*.—Upper side of immature bract: Near RHS Yellow 2C. Under side of immature bract: Near RHS Yellow 2C. Upper side of mature bract: Near RHS Yellow 2C. Under side of mature bract: Near RHS Yellow 2C.
Cyathia:
*Arrangement*.—Involucre of cyathium cup-shaped; 4-lipped, upright.
*Other*.—3 petaloid appendages subtending the cyathia: Height: Approx. 0.3 cm. Diameter: Approx. 0.5 cm. Color Immature: Near RHS Yellow 5A. Color Mature: Near RHS Yellow 5C.
Peduncle:
*Peduncle length*.—Approximately 2.3.
*Peduncle diameter*.—Approximately 1 cm.
*Angle*.—Approximately 45 deg from center of whorl.
*Color*.—Near RHS Greyed-Green 190A.
Pedicils:
*Length*.—Approx. 0.5 cm.
*Diameter*.—Approx. 0.1 cm.
*Angle*.—Near 45 deg. from vertical.
*Strength*.—Strong, flexible.
*Texture*.—Smooth.
*Color*.—Near RHS Greyed-Green 190C.

REPRODUCTIVE ORGANS

Androecium:
*Stamens*.—2 to 4, branched and holding 4 anthers.
*Anther shape*.—Bi-lobed.
*Anther length*.—Approximately 0.05 cm.
*Anther color*.—Near RHS Yellow 5A, Filament colored Yellow 3D.
*Pollen quantity*.—Not observed.
Gynoecium:
*Pistil number*.—1.
*Pistil shape*.—Tri-parted.
*Pistil length*.—Approx. 0.5 cm.
*Style length*.—Approx. 0.2 cm.
*Style color*.—Near RHS 154D.
*Stigma shape*.—Bi-lobed.
*Stigma color*.—Near RHS Yellow 7A.

*Ovary diameter*.—Near RHS 0.2 cm.

*Ovary color*.—Near RHS 154A.

OTHER CHARACTERISTICS

Disease resistance: Neither resistance nor susceptibility to diseases or pests of *Euphorbia characias* has been observed in this variety.

Drought tolerance and cold tolerance: Tender perennial. Tolerates high temperature to at least 32° C. Tolerates low temperatures to −5° C. Drought tolerance has not been measured.

Fruit/seed production: Fruit and seed production not observed to date.

What is claimed is:

1. A new and distinct cultivar of *Euphorbia* plant named 'LAMB01' as herein illustrated and described.

* * * * *